US00PP24104P2

(12) United States Plant Patent
Peters

(10) Patent No.: US PP24,104 P2
(45) Date of Patent: Dec. 17, 2013

(54) ***OMPHALODES* PLANT NAMED 'BLUE EYES'**

(50) Latin Name: ***Omphalodes* hybrid**
Varietal Denomination: Blue Eyes

(76) Inventor: Klaus Peters, Kranenburg (DE)

( * ) Notice: Subject to any disclaimer, the term of this patent is extended or adjusted under 35 U.S.C. 154(b) by 81 days.

(21) Appl. No.: 13/506,620

(22) Filed: May 4, 2012

(51) Int. Cl.
*A01H 5/00* (2006.01)

(52) U.S. Cl.
USPC ..... Plt./461

(58) Field of Classification Search
USPC ..... Plt./461
See application file for complete search history.

*Primary Examiner* — Susan McCormick Ewoldt
(74) *Attorney, Agent, or Firm* — Penny J. Aguirre

(57) ABSTRACT

A new cultivar of *Omphalodes*, 'Blue Eyes', characterized by its large flowers that are blue in color, its foliage that is blue-green in color, and its good heat tolerance, and its cold hardiness to at least U.S.D.A. Zone 6.

2 Drawing Sheets

Botanical classification: *Omphalodes* hybrid.
Cultivar designation: 'Blue Eyes'.

BACKGROUND OF THE INVENTION

The present invention relates to a new and distinct cultivar of *Omphalodes* plant, botanically of hybrid origin and known as *Omphalodes* 'Blue Eyes'. The new cultivar will be referred to hereafter by its cultivar name, 'Blue Eyes'.

'Blue Eyes' was discovered by the Inventor as a whole plant mutation in Gothenborg, Sweden in 2010. The parentage of 'Blue Eyes' is unknown but it thought to be an interspecific hybrid based on its characteristic, however the species is unknown.

Asexual reproduction of the new cultivar was first accomplished under the direction of the Inventor by in vitro propagation in Rijswijk, The Netherlands in 2011. Propagation by has determined that the characteristics of this cultivar are stable and are reproduced true to type in successive generations.

SUMMARY OF THE INVENTION

The following traits have been repeatedly observed and represent the characteristics of 'Blue Eyes'. These attributes in combination distinguish 'Blue Eyes' as a new and distinct cultivar of *Omphalodes*.

1. 'Blue Eyes' exhibits large flowers that are blue in color.
2. 'Blue Eyes' exhibits foliage that is blue-green in color.
3. 'Blue Eyes' exhibits good heat tolerance.
4. 'Blue Eyes' is cold hardy at least to U.S.D.A. Zone 6.

The new cultivar, 'Blue Eyes', is unique from the all other cultivars of *Omphalodes* known to the Inventor. 'Blue Eyes' can be compared to typical plants of the species *Omphalodes verna*, which have greener foliage and smaller flowers. 'Blue Eyes' can also be compared to cultivars of *Omphalodes cappadocica*; 'Starry Eyes' and 'Cherry Ingram' (both unpatented). 'Starry Eyes' differs from 'Blue Eyes' having flowers that are bicolor in blue and white. 'Cherry Ingram' differs from 'Blue Eyes' in having deeper blue colored flowers and lighter green foliage.

BRIEF DESCRIPTION OF THE DRAWING

The accompanying colored photographs illustrate the overall appearance and distinct characteristics of the new *Omphalodes*. The photographs were taken of a six month-old plant of 'Blue Eyes' as grown outdoors in a 1.5-liter container in Kranenburg, Germany.

The photograph in FIG. 1 provides an overall view of a plant of 'Blue Eyes' in bloom.

Figure 1:
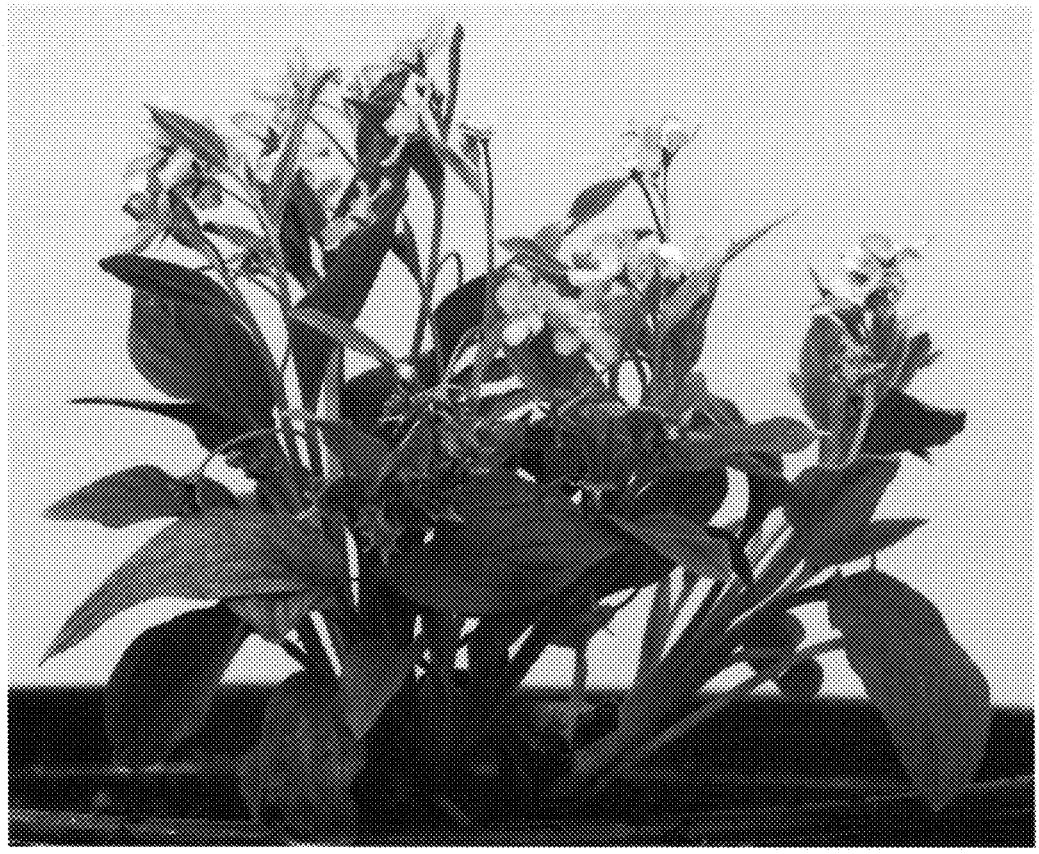
Figure 2:
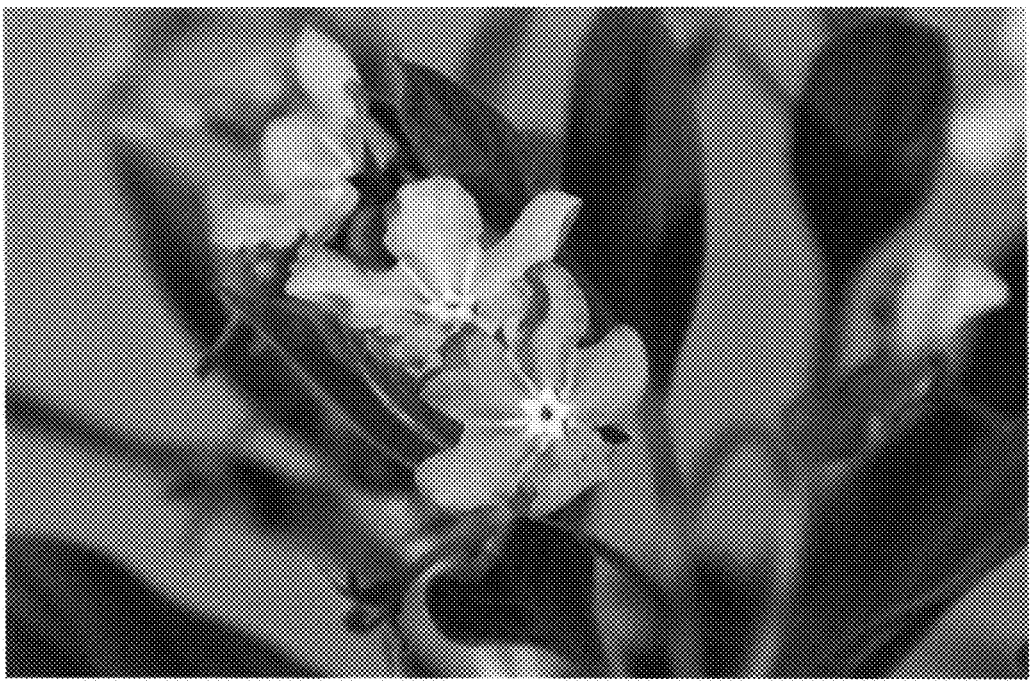

The photograph in FIG. 2 provides a close-up view of the flowers of 'Blue Eyes'.

Figure 3:
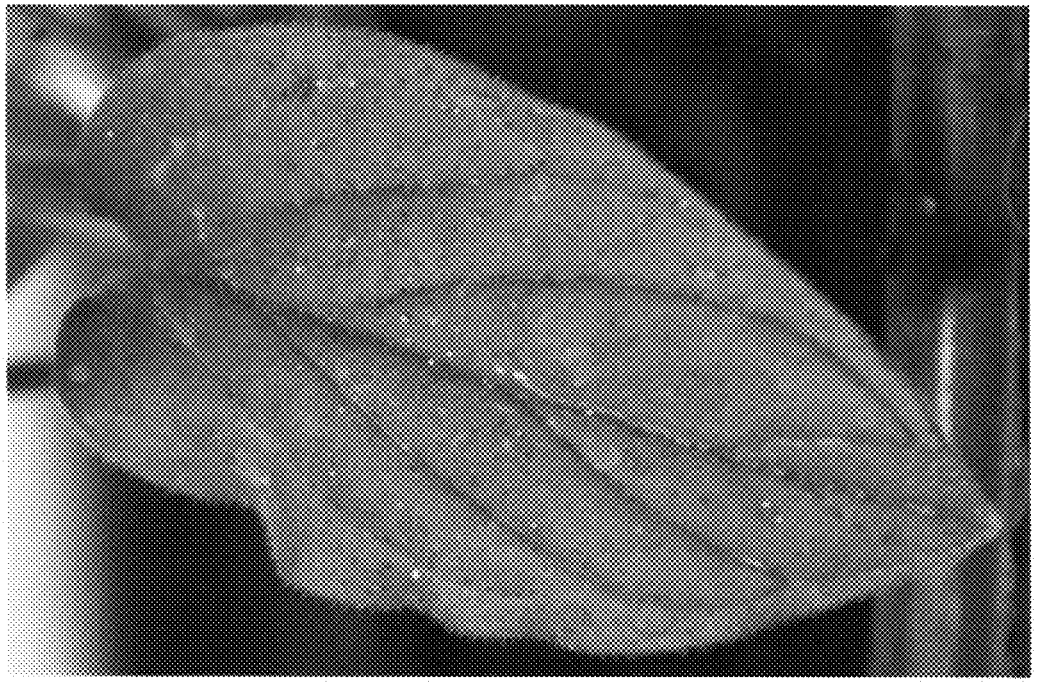

The photograph in FIG. 3 provides a close-up view of the foliage of 'Blue Eyes'.

The colors in the photographs are as close as possible with the photographic and printing technology utilized. The color values cited in the detailed botanical description accurately describe the colors of the new *Omphalodes*.

DETAILED BOTANICAL DESCRIPTION OF THE PLANT

The following is a detailed description of six month-old plants of 'Blue Eyes' as grown outdoors in 1.5-liter containers in Kranenburg, Germany. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Late spring to late summer in Germany.

*Plant habit.*—Herbaceous perennial with an upright and open plant habit.

*Height and spread.*—Reaches 15.8 cm in height and about 17.7 cm in spread.

*Cold hardiness.*—At least to U.S.D.A. Zone 6.

*Heat tolerance.*—Good tolerance has been observed.

*Diseases and pests.*—Not more susceptible to pests and diseases than other varieties of *Omphalodes*.

*Root description.*—Fibrous.

*Growth rate.*—Moderately vigorous.

*Propagation.*—In vitro propagation preferred.

Stem description:

*Stem size.*—Average of 11.8 cm in length and 2 mm in diameter.

*Stem shape.*—Triangular.

*Stem color.*—146C.

*Stem surface.*—Moderately covered with short soft hairs; an average of 1 mm in length, NN155C to NN155D in color.

*Internode length.*—Average of 3.2 cm.

*Branching.*—Moderately branched with an average of 11 lateral branches, held at an average angle of 25° (0°=vertical).

Foliage description:

*Leaf shape.*—Ovate.

*Leaf division.*—Single.

*Leaf base.*—Broad attenuate.

*Leaf apex.*—Acute.

*Leaf venation.*—Pinnate, color: upper surface; 143A, lower surface; 144A to 144B.

*Leaf margins.*—Entire, wavy.

*Leaf attachment.*—Petiolate.

*Leaf arrangement.*—Alternate.

*Leaf surface.*—Moderately covered with pubescence on upper and lower surface with short hairs; an average of 1 mm in length and NN155D in color.

*Leaf color.*—Young leaves upper surface; ranges between 137C and 138A, young leaves lower surface; 138B, mature leaves upper surface; 137A, mature leaves lower surface; 138A to 138B.

*Leaf size.*—Average of 5.4 cm in length and 2.5 cm in width.

*Leaf quantity.*—Average of 4 leaves per lateral branch.

*Petioles.*—Average of 5.4 cm in length and 4 mm in diameter, color: upper and lower surface; 144B, becoming 144A at the distal side and 145C towards the base.

Flower description:

*Inflorescence type.*—Terminal drepanium, monochasial cyme, single, rotate.

*Lastingness of flowers.*—About 7 days.

*Flower size.*—Average of 4.3 cm in height and 3.7 cm in width.

*Flower fragrance.*—Faint, sweet and pleasant.

*Flower number.*—Average of 4 per lateral system.

*Flower aspect.*—Upright.

*Flower buds.*—Broad ovate in shape, average of 5 cm in length and 3.5 mm in diameter, N88C to N88D in color.

*Corolla features.*—Petals are fused near base and rotate in form, slightly cupped.

*Petal number.*—5.

*Petal shape.*—Obovate.

*Petal color.*—Opening upper surface; 100B to 101B, opening lower surface; 100C, fully open upper surface; 101B, fully opened lower surface; 100C.

*Petal surface.*—Upper and lower surface; smooth, dull and very slightly crinkled.

*Petal margins.*—Entire.

*Petal apex.*—Rounded.

*Petal size.*—Average of 8 mm in length and 6 mm in width at the widest part of the petal, 4 mm in width at the base of free (upper) part of petal.

*Calyx form.*—Rotate, 3 mm in length and 8 mm in diameter.

*Sepals.*—5, narrow ovate in shape, average of 5 mm length and 2.5 mm in width, entire margin, narrow acute apex, base fused (lower 10%), dull on upper and lower surface, color young and upper and lower surface; 147C, mature upper and lower surface; 147C, moderately to densely covered with soft short hairs, 1 mm in length and NN155C in color.

*Peduncles.*—Oval in shape, average of 3.1 cm in length and 1 mm in diameter, not very strong, held at about a 0° angle (straight on top of lateral stem), color: upper and lower surface; 146C.

*Pedicels.*—Oval in shape, average of 1.9 cm in length and 1 mm in diameter, not very strong, held at about a 50° angle, color upper and lower surface; 146B to 146C.

Reproductive organs:

*Gynoecium.*—1 pistil, about 1.1 cm in length, stigmas are club-shaped and 145A in color, style is about 1 mm in length and 145B in color, ovary is between 144A and 144B in color.

*Androcoecium.*—5 stamens, anthers are basifixed and ovate in shape, 1 mm in length, and 161D in color, filaments are 0.5 mm in length and N155A in color, pollen is moderate in quantity and 156D in color.

*Fruit/seeds.*—Sterile, seeds are not produced.

It is claimed:

1. A new and distinct cultivar of *Omphalodes* plant named 'Blue Eyes' as herein illustrated and described.

* * * * *